(12) United States Patent
Kroll

(10) Patent No.: US 7,970,465 B1
(45) Date of Patent: Jun. 28, 2011

(54) DECISION PARADIGMS FOR IMPLANTABLE CARDIOVERTER-DEFIBRILLATORS

(75) Inventor: Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 1070 days.

(21) Appl. No.: 11/469,254

(22) Filed: Aug. 31, 2006

(51) Int. Cl.
*A61N 1/39* (2006.01)

(52) U.S. Cl. ......... 607/6; 607/5; 607/7; 607/18; 607/24; 607/23

(58) Field of Classification Search ............. 607/5, 6, 607/18, 23, 24
See application file for complete search history.

(56) References Cited

U.S. PATENT DOCUMENTS

| | | | |
|---|---|---|---|
| 4,774,950 A * | 10/1988 | Cohen | ............................. 607/6 |
| 4,967,749 A | 11/1990 | Cohen | |
| 4,984,572 A | 1/1991 | Cohen | |
| 4,986,270 A | 1/1991 | Cohen | |
| 5,009,234 A * | 4/1991 | Alt | ................................ 600/485 |
| 5,027,816 A * | 7/1991 | Cohen | ............................. 607/4 |
| 5,054,485 A | 10/1991 | Cohen | |
| 5,085,213 A | 2/1992 | Cohen | |
| 5,105,810 A * | 4/1992 | Collins et al. | .................... 607/9 |
| 5,163,429 A | 11/1992 | Cohen | |
| 5,906,633 A * | 5/1999 | Mouchawar et al. | ............. 607/5 |
| 6,575,912 B1 * | 6/2003 | Turcott | ........................ 600/485 |
| 2001/0034488 A1 | 10/2001 | Policker et al. | |

FOREIGN PATENT DOCUMENTS

EP      0317065 B1     12/1994

* cited by examiner

*Primary Examiner* — Carl H Layno
*Assistant Examiner* — Natasha N Patel

(57) ABSTRACT

New decision paradigms for ICDs are described. In one implementation, an implantable system senses cardiac output and arterial pressure parameters and shocks the heart in inverse relation to the arterial pressure, if the cardiac output is insufficient. In another implementation, the implantable system applies atrial anti-tachycardia pacing before applying ventricular anti-tachycardia pacing, if the heart rate is tachycardic.

12 Claims, 6 Drawing Sheets

DECISION PARADIGMS FOR IMPLANTABLE CARDIOVERTER-DEFIBRILLATORS

TECHNICAL FIELD

Subject matter presented herein generally relates to implantable medical devices and more particularly to new decision paradigms for implantable cardioverter-defibrillators (ICDs).

BACKGROUND

Conventional paradigms for deciding when and how an ICD should treat ventricular arrhythmias, such as ventricular fibrillation or ventricular tachycardia, typically rely solely on detection and analysis of cardiac rhythm—including the heart rate. Because these arrhythmias are serious maladies, an unprecedented amount of cost and effort has been dedicated to furthering the arts of detecting and analyzing cardiac rhythms and arrhythmias.

Ventricular fibrillation is a serious condition that often causes sudden cardiac death. In ventricular fibrillation, the heart rate in the ventricles becomes ineffectively rapid because the electrical activity controlling the ventricles becomes chaotic. The heart beats so quickly and chaotically that the ventricles effectively tremble instead of pumping blood. An ICD typically treats ventricular fibrillation by applying a strong electrical shock—defibrillation—that stops all erratic electrical activity allowing a normal cardiac rhythm to ensue.

Ventricular tachycardia occurs when the electrical impulses controlling the ventricles remain orderly but occur far too rapidly to effectively pump blood. Ventricular tachycardia can quickly turn into ventricular fibrillation. If ventricular tachycardia is sensed, an ICD can apply rapidly paced beats—anti-tachycardia pacing (or "ATP")—at a pace that is even more rapid than the tachycardia, thereby overcoming the heart's own abnormal rate. When the artificial pacing is stopped, the heart often returns to a normal rate and rhythm. Sometimes ATP does not work, so a second tier remedy is applied in the form of cardioversion shocks that are timed to coincide with features of the heart's inherent rhythm in order to stop the ventricular tachycardia and bring the rate and rhythm back within normal parameters.

As shown in FIG. 1, the conventional paradigm for making a decision 100 about when and how to apply a treatment, such as ATP, cardioversion, or defibrillation, relies entirely on detection of details of the cardiac rhythm 102. This reliance on the rhythm may have arisen historically, because the first implantable cardiac devices in the 1950's were pacemakers 104 that sought to influence the cardiovascular parameter most amenable to simple electrical control. Evolution of implantable cardiac devices into more sophisticated units still tends to favor detection and analysis of rhythm 102 in making the decision 100 to apply treatment 106 or to continue with no treatment 108—because of rhythm's historical priority.

Rhythm, however, can be a rather one-dimensional parameter for analyzing and then applying control to the entire cardiovascular system, and at times the view it affords of the more comprehensive cardiovascular hemodynamics can be likened to assessing a broad landscape through a limiting pinhole. Cardiac rhythm alone is not always a good indicator of the many nuances of the blood perfusion task that the cardiovascular system is supposed to be performing.

Because of the historical obsession with rhythm, some ICD algorithms try to maintain a patient's actual rhythm in textbook perfection. There are now rhythm detection enhancements, and enhancements to the enhancements. The attempt to maintain rhythm perfection, however, and the reliance on only rhythm to indicate the state of the cardiovascular system has its downside. Actual shock treatment following false alarms, and over-treatment of transient arrhythmias are side effects of this tendency to agonize over the rhythm. These side effects and "mis"-treatments are very disconcerting to a patient and have been known to cause feelings of helplessness and resignation and even actual depression. It is disconcerting to realize that one's implanted cardiac device has developed a mind of its own and is randomly applying surprising and painful shocks.

A reliance on rhythm as the input for ICD treatment decisions also fails to provide the best cost versus benefit tradeoff to developers and patients. Some of the rhythm detection enhancements of conventional ICDs are extravagant and exotic, raising the unit cost of development and production, but often failing to save the patient from occurrence of the inappropriate shocks and other side effects. Decision trees implemented by conventional ICDs are lacking at times in favorable cost/benefit tradeoffs for the patient. A particular treatment decision made by a conventional ICD may cost the patient a great deal of pain to keep the rhythm perfect but not benefit the patient that much, on a common sense level.

Using other hemodynamic parameters in the ICD's decision-making process might give superior results by giving the patient a more reasonable cost/benefit tradeoff between pain and actual physiological well-being.

SUMMARY

New decision paradigms for ICDs are described. In one implementation, an implantable system senses cardiac output and arterial pressure parameters and shocks the heart in inverse relation to the arterial pressure, if the cardiac output is insufficient. In another implementation, the implantable system applies atrial anti-tachycardia pacing before applying ventricular anti-tachycardia pacing, if the heart rate is tachycardic.

DETAILED DESCRIPTION

Overview

Figure 1:
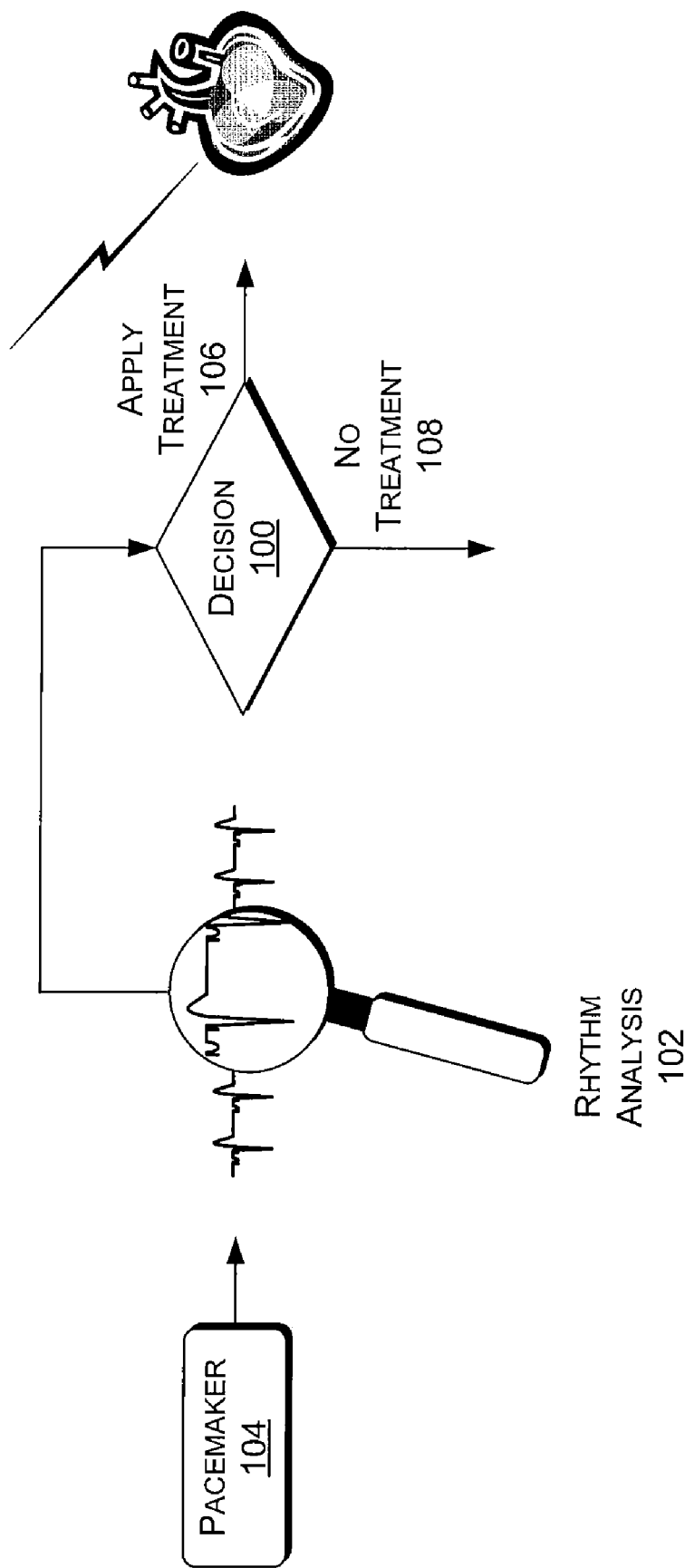
FIG. 1 is a diagram illustrating conventional techniques for deciding a treatment for ventricular arrhythmias.

The following discussion describes exemplary new decision paradigms for ICDs. Exemplary paradigms described herein enjoin other cardiovascular and hemodynamic parameters besides just cardiac rhythm for the decision-making processes that occur onboard an ICD.

Conventional ICDs have detection schemata that agonize over detecting and analyzing cardiac rhythm to ensure that detection of potentially lethal ventricular fibrillation is never missed and to try to minimize inappropriate shocks that are usually horribly disturbing to patients. In spite of all of these precautions, approximately one in three patients receives inappropriate shocks and approximately one in three suffers from anxiety and depression as a result of the inappropriate shocks.

Some of the more recent innovations in low-pain waveforms and hemodynamics sensing, such as innovative arterial pressure sensors and innovative cardiac output sensors allow the possibility of changing and even superceding conventional rhythm detection rules. In exemplary paradigms presented herein, the use of rate as a primary detector is ignored entirely or at least minimized. This allows a departure from the conventional "Byzantine" rate detection rules.

A critical element of the exemplary detection paradigms is that rather than fostering a preoccupation with the rhythm, decision branches consider other hemodynamic parameters and select therapies based on balancing the cost/benefit tradeoff of each therapy. That is, a primary concept for each decision branch in exemplary decision-making processes is first, to achieve a satisfactory knowledge of the hemodynamics, and then, to choose therapies on the basis of a good balance between the cost entailed (e.g., to the patient) versus the benefit provided.

This type of exemplary "detection" schema essentially ignores the conventional rhythm/rate parameter or treats it only as a secondary diagnostic. In fact, these exemplary paradigms are more aptly described as "decision" approaches as opposed to "detection" approaches because they are not preoccupied with an exact detection of the rhythm.

The cardiovascular system, like any other fluid pumping circuit, has many other parameters to be considered besides the pump rate and/or rhythm, such as: pumping force, pump stroke volume, pump output per unit time, system fluid volume, vessel length and diameter, fluid pressure, etc. Accordingly, many maladies such as hypertension, for example, are best treated not by sensing and controlling the rhythm parameter, but by altering other parameters, e.g., increasing or decreasing the pump strength by medications, removing fluid volume from the system via diuretics, increasing the diameter of the vessels with calcium channel blockers, etc.

In the case of an ICD, some of these cardiovascular and hemodynamic parameters are inherently better than others as indicators for gauging the effectiveness of the oxygen perfusion and carbon dioxide balancing tasks that the cardiovascular system is supposed to be performing. For example, a direct measure of cardiac output (CO) is superior to many types of rhythm measurements. Often, cardiac output describes directly what the rhythm is perhaps describing only indirectly. In other words, if the cardiac output is satisfactory, the rhythm is also satisfactory almost by definition, or put differently, if the cardiac output is sufficient, then for many practical purposes, the rhythm does not really matter.

Arterial pressure is blood pressure, defined as the force applied to a unit area of surface of a blood vessel. Blood pressure is usually understood to mean arterial blood pressure, i.e. the pressure in the large arteries. The pressure of the blood in other vessels is lower than the arterial pressure. Cardiac output is defined as the volume of blood that is pumped by the heart per unit time, usually measured in liters per minute. Stroke volume is the volume of blood pumped out by the left ventricle in one contraction and when multiplied by the heart rate yields the cardiac output. An adult human heart typically pumps approximately 5 liters of blood per minute.

Figure 2:
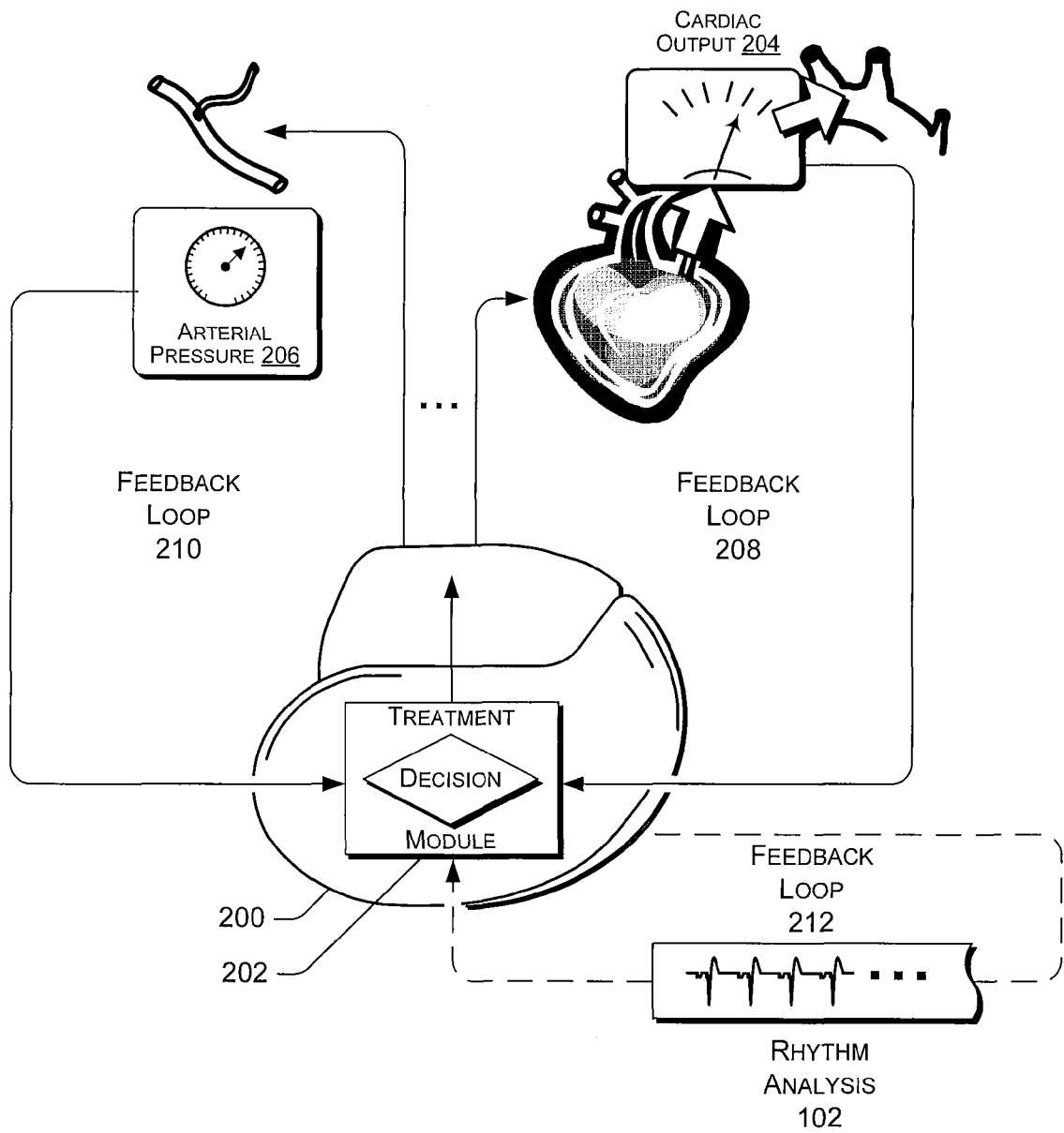
FIG. 2 is a diagram of an exemplary ICD system that makes treatment decisions based on multiple hemodynamic parameters.

FIG. 2 shows an exemplary ICD 200 that uses different cardiovascular and hemodynamic parameters than just rhythm to make treatment decisions 202. In this example, the sensing of cardiac output 204 and arterial pressure 206 are incorporated into respective feedback loops (208, 210) with the ICD 200 in order to provide more robust self-regulating treatment decisions 202 than just relying on rhythm detection and rhythm analysis alone. In one implementation, the exemplary ICD 200 optionally accepts analysis of rhythm 102 also, perhaps in an ancillary or second tier feedback circuit 212. For example, cardiac output can be sensed by the use of impedance techniques, which measure the volume of a heart chamber or distension in the aorta from the increased cardiac output as taught, for example, in U.S. Pre-Grant Patent Publication No. 20020002389 to Kerry Bradley et al, entitled, "Cardiac stimulation devices and methods for measuring impedances associated with the left side of the heart," the disclosure of which is incorporated by reference herein. Aortic pressure can be estimated from a combination of right ventricular pressure and photoplethysmography.

By monitoring more comprehensive hemodynamic parameters than just rhythm, the exemplary ICD 200 achieves a more stable and comprehensive overview of the patient's cardiovascular state than can be obtained by monitoring a single narrow parameter. With these multiple assessments of several aspects of the patient's current state, the exemplary ICD 200 obtains stability of overview and can be more lenient (or more aggressive, as the case may be) in treating a deviance in one particular sensed parameter. This is because the ICD 200 can ignore the one suspect parameter and rely on alternate parameters to triangulate the correct state of the patient. This allows the exemplary ICD 200 to refrain from forcing treatment of certain false alarms that result in unpleasant side effects for the patient.

In other words, conventional ICDs 104 are focused on just one narrow parameter, such as rhythm, and when the one parameter deviates, the conventional ICD 104 has no choice but to take the deviance seriously as a bona fide pathology and treat it, even though later it may turn out that the deviance was a transient or harmless state that did not require treatment. The exemplary ICD 200, however, with an eye on multiple indicators at once, is more capable of sensing when a deviant parameter merely represents noise or a transient, harmless deviancy.

The combination of sensing cardiac output 204 and sensing arterial pressure 206, moreover, provides a particularly effective indicator of the patient's overall cardiovascular state. For example, if both the cardiac output 204 and the arterial pressure 206 are both within a normal range, then it is very difficult to conclude that the heart is not performing its blood circulation task properly. In such a case, it would also be difficult to conclude, for example, that the onset of a mild arrhythmia requires urgent treatment. Because of this increase in the sophistication of decision-making power afforded by using multiple non-rhythm parameters, the exemplary ICD 200 is a step closer to obtaining from a machine, safer, enlightened, and reasonable diagnoses and treatments than obtainable from conventional ICDs 104.

By using one or more non-rhythm hemodynamic parameters in decision-making processes 202, more refined and nuanced decision-making techniques and algorithms can be implemented by the exemplary ICD 200, as will be described more fully below in the "Exemplary Methods" section.

Exemplary Implantable Device

Figure 3:
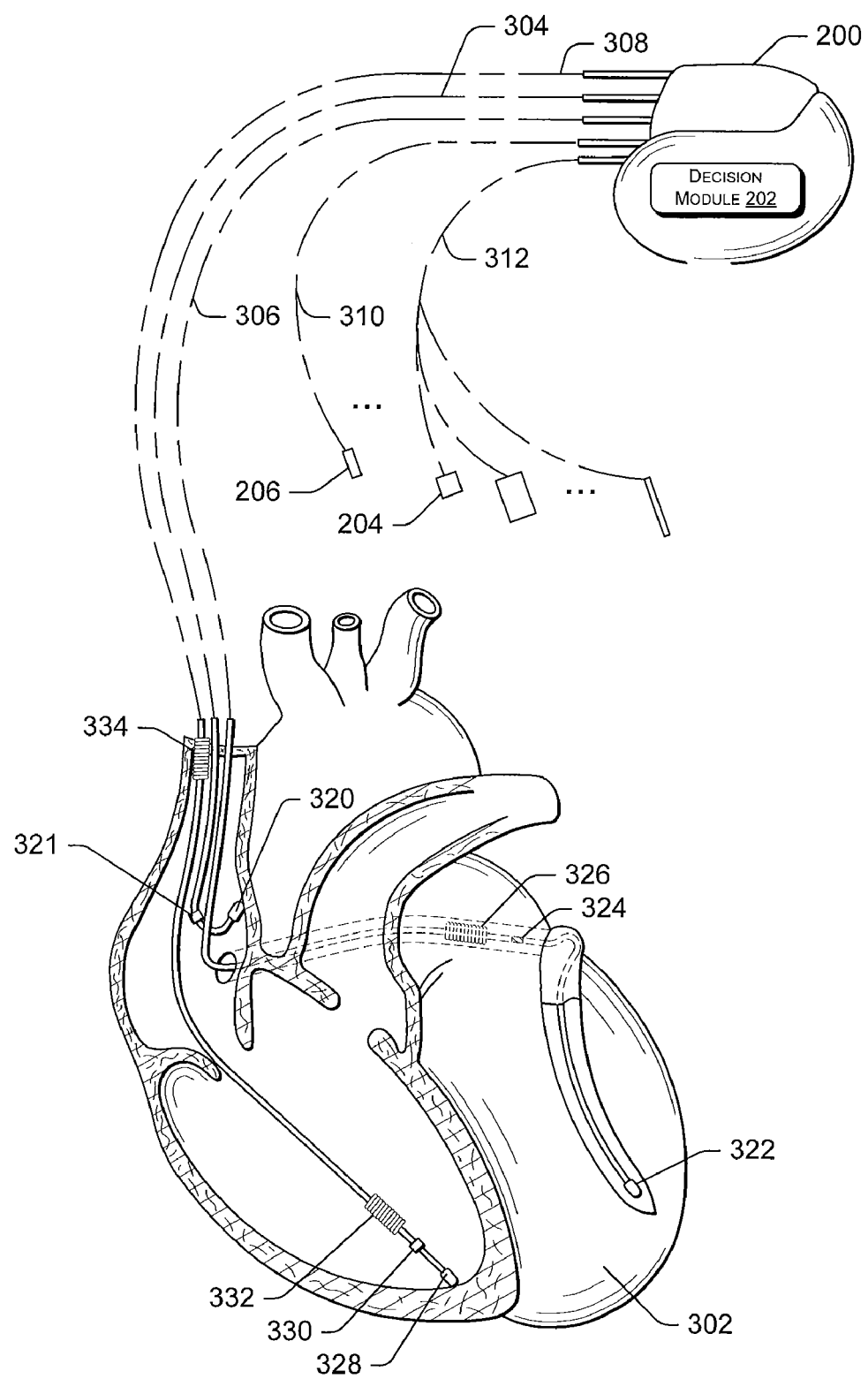
FIG. 3 is a diagram of the exemplary ICD of FIG. 2 in relation to a human heart.

FIG. 3 shows an exemplary implementation of the ICD 200 introduced above in electrical communication with a human heart 302 and other bodily tissues. The illustrated configuration is only an example. Such an exemplary ICD 200 can be characterized as a miniature computing device that is implanted into the body to monitor, regulate, and/or correct cardiovascular and other activities. The ICD 200 typically applies stimulation therapy to the heart and may perform other cardiovascular therapies.

In the illustrated implementation, three of the electrical leads—a right atrial lead 304, a coronary sinus lead 306, and a right ventricular lead 308—interconnect the ICD 200 with the heart 302 to support multi-chamber detection and stimulation therapy. One or more physiological sensor leads (310, . . . , 312) may also be employed to position physiological sensors within the body, such as cardiac output sensor 204 and arterial pressure sensor 206. In the case of an arterial blood pressure sensor 206, a photoplethysmograph (PPG) infrared light sensor may be coupled to the physiological sensor lead 310.

The right atrial lead 304 may support an atrial tip electrode 320, which is typically implanted in a patient's right atrial appendage. The right atrial lead 304 also supports a right atrial ring electrode 321, which enables the device to sense atrial cardiac signals and apply pacing therapy to the right atrial chamber.

The coronary sinus lead 306 may position a left ventricular tip electrode 322 adjacent to the left ventricle and/or additional electrode(s) adjacent to the left atrium, such as a left atrial ring electrode 324 and a left atrial coil electrode 326. The coronary sinus lead 306 enables the exemplary ICD 200 to sense left atrial and ventricular cardiac signals and administer left chamber pacing therapy. In the illustrated arrangement, the left ventricular tip electrode 322 is used to sense atrial and ventricular cardiac signals and can be used to deliver left ventricular pacing therapy. The left atrial ring electrode 324 can be employed for applying left atrial pacing therapy, and the left atrial coil electrode 326 may be used for applying shocking therapy.

The right ventricular lead 308 is electrically coupled to a right ventricular tip electrode 328, a right ventricular ring electrode 330, a right ventricular (RV) coil electrode 332, and a superior vena cava (SVC) coil electrode 334. Typically, the right ventricular lead 308 is transvenously inserted into the heart 302 to place the right ventricular tip electrode 328 in the right ventricular apex so that the RV coil electrode 332 will be positioned in the right ventricle and the SVC coil electrode 334 will be positioned in the superior vena cava. Accordingly, the right ventricular lead 308 is capable of receiving cardiac signals, and delivering stimulation in the form of pacing and shock therapy to the right ventricle.

Figure 4:
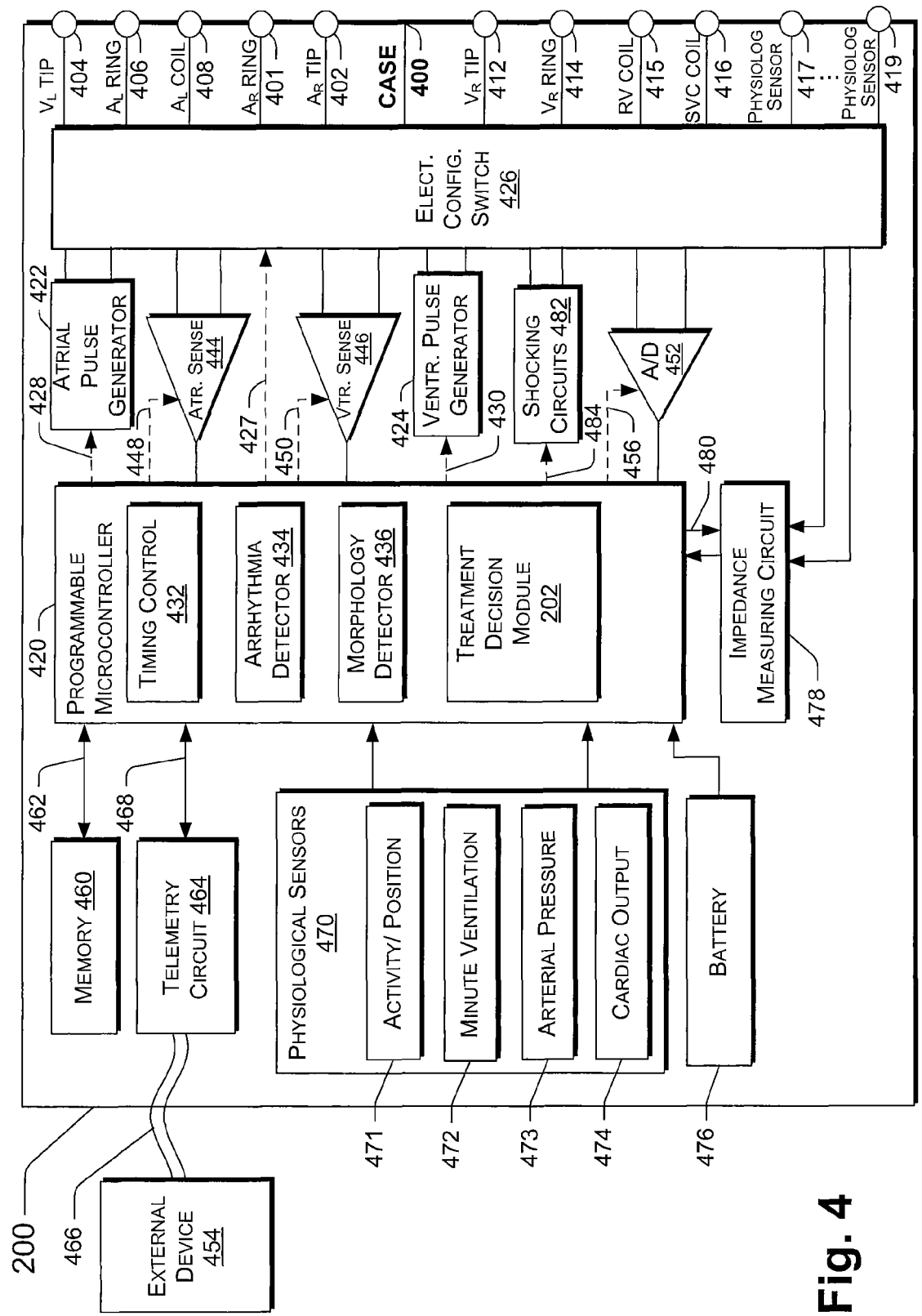
FIG. 4 is a block diagram of components of the exemplary ICD of FIGS. 2 and 3.

FIG. 4 shows an exemplary block diagram depicting various components of the ICD 200. The components are typically contained in a case 400, which is often referred to as the "can", "housing", "encasing", or "case electrode", and may be programmably selected to act as the return electrode for unipolar operational modes. The case 400 may further be used as a return electrode alone or in combination with one or more of the coil electrodes 326, 332 and 334 for stimulating purposes. The case 400 further includes a connector (not shown) having a plurality of terminals (401, 402, 404, 406, 408, 412, 414, 415, 416, 417, and 419—shown schematically with the names of the electrodes to which they are connected shown next to the terminals), including:

a right atrial ring terminal (AR RING) 401 for atrial ring electrode 321;

a right atrial tip terminal (AR TIP) 402 for atrial tip electrode 320;

a left ventricular tip terminal (VL TIP) 404 for left ventricular tip electrode 322;

a left atrial ring terminal (AL RING) 406 for left atrial ring electrode 324;

a left atrial shocking terminal (AL COIL) 408 for left atrial coil electrode 326;

a right ventricular tip terminal (VR TIP) 412 for right ventricular tip electrode 328;

a right ventricular ring terminal (VR RING) 414 for right ventricular ring electrode 330;

a right ventricular shocking terminal (RV COIL) 415 for RV coil electrode 332;

an SVC shocking terminal (SVC COIL) 416 for SVC coil electrode 334;

a physiological sensor terminal 417 for physiological sensor lead 312 and arterial pressure sensor 206; and an "nth" physiological sensor terminal 419 for physiological sensor lead 310 and an "nth" physiological sensor, such as cardiac output sensor 204.

An exemplary ICD 200 may include a programmable microcontroller 420 that controls various operations of the ICD 200, including cardiovascular monitoring, hemodynamic monitoring, and cardiovascular stimulation therapy. Microcontroller 420 includes a microprocessor (or equivalent control circuitry), RAM and/or ROM memory, logic and timing circuitry, state machine circuitry, and I/O circuitry.

The exemplary ICD 200 may further include an atrial pulse generator 422 and a ventricular pulse generator 424 that generate pacing stimulation pulses for delivery by the right atrial lead 304, the coronary sinus lead 306, and/or the right ventricular lead 308 via an electrode configuration switch 426. The electrode configuration switch 426 may include multiple switches for connecting the desired electrodes to the appropriate I/O circuits, thereby providing complete electrode programmability. Accordingly, switch 426, in response to a control signal 427 from the microcontroller 420, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 422 and 424 may include dedicated, independent pulse generators, multiplexed pulse generators, or shared pulse generators. The pulse generators 422 and 424 are controlled by the microcontroller 420 via appropriate control signals 428 and 430, respectively, to trigger or inhibit the stimulation pulses.

Microcontroller 420 is illustrated as including timing control circuitry 432 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 420 may also implement an arrhythmia detector 434, a morphology detector 436, and an exemplary treatment decision module 202. The treatment decision module 202 in turn can process input from physiological sensors 470, such as accelerometers of an activity/position module 471, a minute ventilation module 472, an arterial pressure module 473, a cardiac output module 474, etc., diagnose cardiovascular disturbances, make treatment decisions generally without considering the cardiac rhythm, and provide cardiovascular therapies. The therapies may compensate for detected cardiovascular disturbances using ongoing feedback from the physiological sensors 470. The treatment decision module 202 can also use rhythm/rate input is some implementations.

The components 434, 436, and 202 may be implemented in hardware as part of the microcontroller 420, or as software/firmware instructions programmed into an implementation of the ICD 200 and executed on the microcontroller 420 during certain modes of operation. Although not shown, the microcontroller 420 may further include other dedicated circuitry and/or firmware/software components that assist in monitoring various conditions of the patient's heart and managing pacing therapies.

Atrial sensing circuits 444 and ventricular sensing circuits 446 may also be selectively coupled to the right atrial lead 304, coronary sinus lead 306, and the right ventricular lead 308, through the switch 426 to detect the presence of cardiac activity in each of the four chambers of the heart. The sensing circuits 444 and 446 may include dedicated sense amplifiers, multiplexed amplifiers, or shared amplifiers. Switch 426 determines the "sensing polarity" of the cardiac signal by selectively closing the appropriate switches. In this way, the clinician may program the sensing polarity independent of the stimulation polarity.

Each sensing circuit 444 and 446 may employ one or more low power precision amplifiers with programmable gain and/or automatic gain control, bandpass filtering, and a threshold detection circuit to selectively sense the cardiac signal of interest. The automatic gain control enables the exemplary ICD 200 to sense low amplitude signal characteristics of atrial or ventricular fibrillation.

The outputs of the atrial and ventricular sensing circuits 444 and 446 are connected to the microcontroller 420 which, in turn, is able to trigger or inhibit the atrial and ventricular pulse generators 422 and 424 in a demand fashion in response to the absence or presence of cardiac activity in the appropriate chambers of the heart. The sensing circuits 444 and 446 receive control signals from the microcontroller 420 over signal lines 448 and 450 to control, for example, the gain and/or threshold of polarization charge removal circuitry (not shown) and the timing of blocking circuitry (not shown) optionally coupled to the inputs of the sensing circuits 444, 446.

Cardiac signals are supplied to an analog-to-digital (A/D) data acquisition system 452, which is configured to acquire intracardiac electrogram signals, convert the raw analog data into a digital signal, and store the digital signals for later processing and/or telemetric transmission to an external device 454. The data acquisition system 452 is coupled to the right atrial lead 304, the coronary sinus lead 306, and the right ventricular lead 308 through the switch 426 to sample cardiac signals across any pair of desired electrodes.

The data acquisition system 452 is coupled to the microcontroller 420, or other detection circuitry, to assist in detecting an evoked response from the heart 302 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 420 detects a depolarization signal during a window following a stimulation pulse, the presence of which indicates that capture has occurred. The microcontroller 420 enables capture detection by triggering the ventricular pulse generator 424 to generate a stimulation pulse, starting a capture detection window using the timing control circuitry 432 within the microcontroller 420, and enabling the data acquisition system 452 via control signal 456 to sample the cardiac signal that falls in the capture detection window and, based on the amplitude, determines if capture has occurred.

The microcontroller 420 is further coupled to a memory 460 by a suitable data/address bus 462. The programmable operating parameters used by the microcontroller 420 are stored in memory 460 and used to customize the operation of the exemplary ICD 200 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 302 within each respective tier of therapy.

The operating parameters of the exemplary ICD 200 may be non-invasively programmed into the memory 460 through a telemetry circuit 464 in telemetric communication via communication link 466 with the external device 454, such as a programmer, local transceiver, or a diagnostic system analyzer. The microcontroller 420 can activate the telemetry circuit 464 with a control signal 468. The telemetry circuit 464 allows intracardiac electrograms and status information relating to the operation of the exemplary ICD 200 (as contained in the microcontroller 420 or memory 460) to be sent to the external device 454 through an established communication link 466.

The physiological sensors 470 referred to above can further include, for example, "rate-responsive" sensors that adjust pacing stimulation rates according to the exercise state of the patient. Accordingly, the microcontroller 420 responds by adjusting the various pacing parameters (such as rate, AV Delay, V-V Delay, etc.) at which the atrial and ventricular pulse generators 422 and 424 generate stimulation pulses.

The physiological sensors 470 may include mechanisms and sensors to detect bodily movement (471), minute ventilation 472, changes in blood pressure 473, changes in cardiac output 474, changes in the physiological condition of the heart, diurnal changes in activity (e.g., detecting sleep and wake states), G-force acceleration of the ICD case 400, length of the cardiac QT interval, blood oxygen saturation, blood pH, changes in temperature, respiration rate, and QRS wave duration. While shown as being included within the exemplary ICD 200, the physiological sensor(s) 470 may also be external to the exemplary ICD 200, yet still be implanted within or carried by the patient, e.g., a blood pressure probe. Examples of physiological sensors external to the case 400 that may be deployed by ICD 200 include sensors that, for example, sense respiration activities, $O_2$ saturation, evoked response, pH of blood, and so forth.

The illustrated physiological sensors 470 include one or more activity/position sensors 471 (e.g., 1D or 3D accelerometers, movement sensors, etc.) to detect changes in the patient's position. The activity/position sensors 471 can be used by the treatment decision module 202 to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up). In response to the detected postural change, a treatment decision module 202 may evaluate blood pressure to see if there has been a decrease in the blood pressure sustained for a duration that is longer than that which usually transpires before a healthy baroreceptor reflex intervenes. The treatment decision module 202 may then administer one or more vascular and/or pacing therapies to reduce the orthostatic hypotension.

In one configuration, accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

Other illustrated physiological sensors 470, as noted, include an arterial pressure module 473 to manage input from an arterial pressure sensor 206, such as a photoplethysmograph (PPG) infrared light sensor surface mounted on the case 400 or otherwise external to the ICD 200. In general, signals generated by the physiological sensors 470 can be passed to the microcontroller 420 for analysis by the treatment decision module 202. Such signals can be used to determine a current state of various hemodynamic parameters to be used in exemplary decision-making techniques that do not rely on cardiac rate and rhythm, or rely on cardiac rhythm only secondarily, as described more fully below with respect to FIGS. 5 and 6. The signals can also indicate whether the patient is at rest, whether the patient is experiencing an episode of cardiovascular disturbance, such as orthostatic hypotension, and can assist in making decisions to invoke a responsive therapy prescribed by the treatment decision module 202.

The minute ventilation (MV) sensor 472 may also be included in the physiological sensors 470 in order to sense rate and depth of breathing. Minute ventilation can be measured as the total volume of air that moves in and out of a patient's lungs in a minute. The MV sensor 472 may use an impedance measuring circuit 478 to sense air movement by measuring impedance across the chest cavity.

The impedance measuring circuit 478 is enabled by the microcontroller 420 via a control signal 480 and can be used for many things besides the abovementioned detection of air movement in and out of the lungs, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 478 may be coupled to the switch 426 so that any desired electrode may be used.

The exemplary ICD 200 additionally includes a battery 476 that provides operating power to all of the components shown in FIG. 4. The battery 476 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 476 also desirably has predictable discharge characteristics so that elective replacement time can be detected. As one example, the exemplary ICD 200 employs lithium/silver vanadium oxide batteries.

The exemplary ICD 200 can further include magnet detection circuitry (not shown), coupled to the microcontroller 420, to detect when a magnet is placed over the exemplary ICD 200. A magnet may be used by a clinician to perform various test functions of the exemplary ICD 200 and/or to signal the microcontroller 420 that an external programmer (e.g., 454) is in place to receive or transmit data to the microcontroller 420 through the telemetry circuits 464.

As an implantable cardioverter/defibrillator device, the exemplary ICD 200 may use the treatment decision module 202 to weigh whether the occurrence of an arrhythmia merits a treatment and if it does, then automatically applies an appropriate electrical pacing or shock therapy to the heart aimed at terminating the detected arrhythmia. To this end, the microcontroller 420 further controls a shocking circuit 482 via a control signal 484. The shocking circuit 482 generates shocking pulses of low (e.g., up to 0.5 joules), moderate (e.g., 0.5-10 joules), or high energy (e.g., 11 to 40 joules), as selected by the microcontroller 420. Such shocking pulses are applied to the patient's heart 302 through at least two shocking electrodes selected, for example, from the left atrial coil electrode 326, the RV coil electrode 332, and/or the SVC coil electrode 334. As noted above, the case 400 may act as an active electrode in combination with the RV electrode 332, or as part of a split electrical vector using the SVC coil electrode 334 or the left atrial coil electrode 326 (i.e., using the RV electrode as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 420 is capable of controlling the synchronous or asynchronous delivery of the shocking pulses.

More generally, the exemplary ICD 200 can be programmed to stimulate different sets of vascular and cardiac muscles through the same lead/electrode system. The exemplary ICD 200 can be programmed to vary the output voltage of various pulses to effectively stimulate different muscles of the heart and blood vessels, even though the lead and electrode placement does not change.

Exemplary Methods

Figure 5:
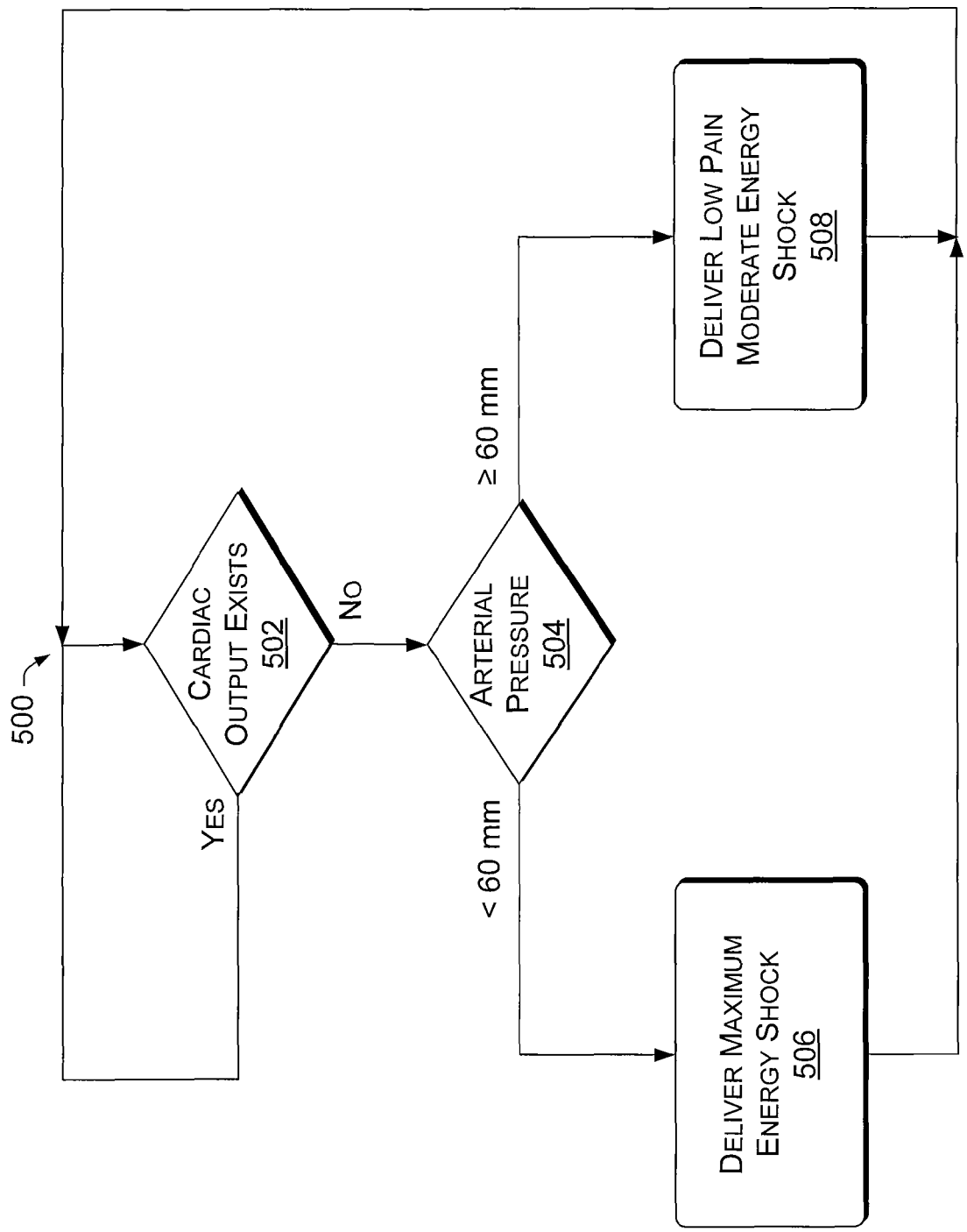
FIG. 5 is a flow diagram of an exemplary method of making treatment decisions without relying on detection of cardiac rhythm.

FIG. 5 shows an exemplary method 500 of making a treatment decision without relying on cardiac rhythm. The exemplary method 500 may be implemented in connection with many suitably configured ICD devices, although it will be described as being executed by the exemplary treatment decision module 202 of the exemplary ICD 200. In the flow diagram of FIG. 5, the operations are summarized in individual blocks. Some operations may be performed in hardware and/or as machine-readable instructions (software or firmware) that can be executed by a processor, such as microcontroller 420.

At block 502, the existence of cardiac output is monitored, for example, as detected by a cardiac output sensor 204. If there is cardiac output (i.e., the "Yes" branch from block 502), cardiac output continues to be monitored as represented by the return loop.

If there is no cardiac output (i.e., the "No" branch from block 502), the exemplary method 500 considers the arterial pressure, e.g., as detected by an arterial pressure sensor 206 (block 504). A threshold level for the arterial pressure can be predetermined on a patient-by-patient basis. Suppose for one patient, for example, the threshold level is 60 millimeters of mercury (mmHg). Accordingly, if the arterial pressure is (on average) less than 60 millimeters of mercury (mmHg) (i.e., the "<60 mm" branch from block 504), the exemplary method 500 assumes or concludes that the patient has lost consciousness and immediately delivers a maximum energy shock (block 506). This is because at block 504, the method 500 has concluded that there is no cardiac output and the arterial pressure is below the predetermined threshold for this patient. Even without specifically considering the rhythm, this combination of no cardiac output and low arterial pressure calls for a high energy shock, e.g., because ventricular fibrillation or ventricular tachycardia has made pumping cease or become grossly ineffective.

Returning to block 504, if the arterial pressure is greater than or equal to 60 mmHg (i.e., the "≧60 mm" branch from block 504), the exemplary method 500 assumes or concludes that the patient has not lost consciousness and delivers a low pain, moderate energy shock (block 508). From each shock—maximum energy at block 506 and low pain moderate energy at block 508—the process returns to block 502 to monitor the cardiac output to determine if either shock had effect. In other words, the beginning block 502 of the method 500 is also the assessment block for checking the results of the treatment blocks 506 or 508 executed during a previous cycle of the method 500. If the moderate energy shock (block 508) was truly ineffective, then the exemplary method 500 is self-regulating due to the physiological feedback loops (208, 210) illustrated in FIG. 2. That is, in the event of an ineffective moderate energy shock (block 508), the arterial pressure 206 eventually falls below the exemplary threshold of 60 mmHg, and the method 500 delivers the high energy shock (block 506) during a subsequent cycle.

The exemplary method 500 may be performed by an exemplary treatment decision module 202 that does not rely heavily or at all on detection and analysis of cardiac rhythm. The exemplary method 500 maintains the patient's life even in the presence of hemodynamically compromising ventricular tachycardia or ventricular fibrillation, yet there is no reliance on a heart rate sensor. Thus, the exemplary method 500 circumvents both simple and complicated heart rate detection sensors (and analyses) including the more "baroque" detection enhancements.

Figure 6:
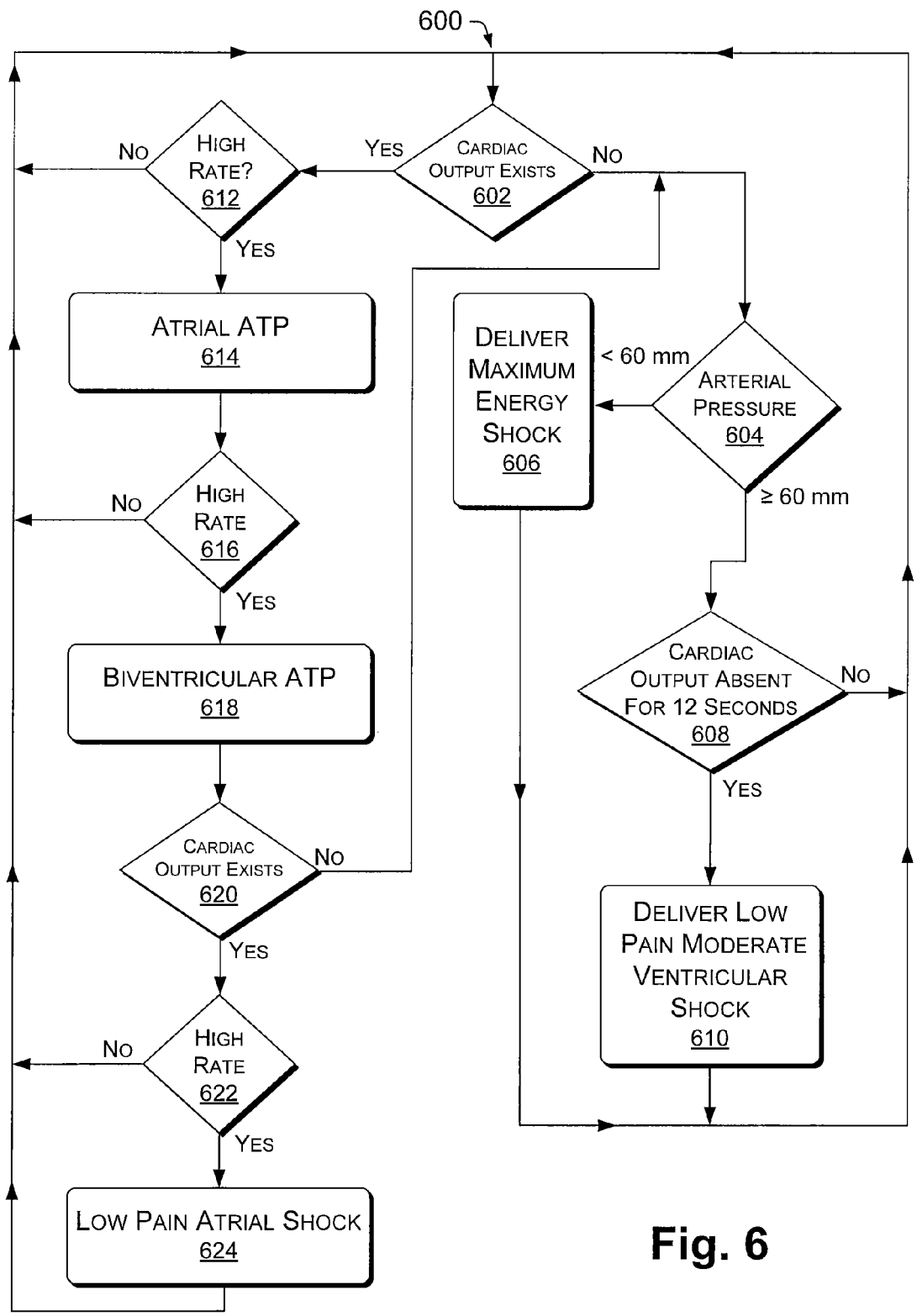
FIG. 6 is a flow diagram of an exemplary method of making treatment decisions using cardiac rhythm merely as a secondary criterion.

FIG. 6 shows an exemplary method 600 of making a treatment decision that includes the detection of cardiac rates as a secondary criterion in order to treat arrhythmias that are not fatal but are merely disturbing to the patient. Cardiac rate provides an adjunct decision-making criterion, as shown in feedback loop 212 of FIG. 2.

The exemplary method 600 may be implemented in connection with many suitably configured ICD devices, although it will be described as being executed by the exemplary treatment decision module 202 of the exemplary ICD 200. In the flow diagram of FIG. 6, the operations are summarized in individual blocks. Some operations may be performed in hardware and/or as machine-readable instructions (software or firmware) that can be executed by a processor, such as microcontroller 420.

At block 602, the exemplary method 600 begins by considering the existence of cardiac output. If there is no cardiac output (the "No" branch from block 602), then the method 600 proceeds to consideration of arterial pressure (block 604). But if cardiac output is present, then the method 600 considers the cardiac rate (block 612), which is discussed further below.

At block 604, in checking the arterial pressure, if the arterial pressure is less than 60 mmHg, for example, then the process proceeds directly to delivery of a maximum energy shock (block 606). The high energy shock is administered because of the combination of no cardiac output (block 602) and arterial pressure below a safe threshold (block 604). After the maximum energy shock, the process loops back (block 602) to check for effectiveness of the shock. If the pressure is greater than or equal to 60 mmHg, for example, then the process considers how long the cardiac output has been absent (block 608).

At block 608, since the arterial pressure is greater than 60 mmHg, for example, the method 600 assumes or concludes that the patient is conscious but may be fainting and very uncomfortable. In one implementation, the method 600 allows the cardiac output to be absent for only approximately 12 seconds. If the cardiac output has been absent for more than approximately 12 seconds, then the method 600 proceeds to deliver a low pain, moderate energy shock (block 610). In other implementations, the method 600 may allow the cardiac output to be absent for as long as some predefined threshold (e.g., 20 seconds) before applying a treatment.

At block 610, when the method 600 delivers the low pain, moderate energy shock in response to the cardiac output being absent for the specified time period, the shock may consist of a 300 volt pulse to the ventricle, for example. In one implementation, the shock is administered between the RV coil 332 and the can or case 400. After the moderate energy shock, the process loops back (block 602) to check the effectiveness of the shock.

During assessment of cardiac output at block 602, if cardiac output is present (the "Yes" branch from block 602), then the process considers the cardiac rate (block 612). If there is a higher than normal cardiac rate, the method 600 begins progressive treatment (block 614) beginning with a safest-treatment-first approach.

At block 614, the method 600 assumes that the higher than threshold rate is due to an atrial arrhythmia. Because the treatment for atrial arrhythmia is the safest treatment in a hierarchy of treatments, it is applied first to see if the least invasive treatment cures the condition. Thus, at block 614, atrial anti-tachycardia pacing (atrial ATP) is applied. The worst-case complication of applying atrial ATP is merely that its application can very rarely induce relatively benign atrial fibrillation. On the other hand, application of ventricular ATP often induces dangerous ventricular fibrillation. So ventricular ATP is avoided until after atrial ATP has been tried, even though the exemplary process may not be aware at this point whether the high heart rate is an atrial or a ventricular rhythm.

At block 616, the method 600 subsequently checks for a higher than threshold heart rate, i.e., whether the application of atrial ATP at block 614 was successful. If there is still a high heart rate, then the method 600 proceeds to the more aggressive ventricular ATP, such as biventricular ATP (block 618), but if the high heart rate has ceased, then the process loops back to monitor the cardiac output (block 602).

At block 620, after applying ventricular ATP at block 618, the process monitors the cardiac output afresh. If there is a loss of cardiac output (the "No" branch from block 620), then the method 600 assumes that application of ventricular ATP has either exacerbated a ventricular tachycardia condition into a higher rate ventricular tachycardia, or has induced a ventricular fibrillation condition. Each of these conditions may cause the cardiac output to cease. Thus, if no cardiac output exists the method 600 proceeds to the arterial pressure sensing branch of the exemplary process (block 604). But if there is still cardiac output after application of the ventricular ATP at block 618, then the method 600 assesses the heart rate yet again (block 622).

At block 622, if the high heart rate has normalized, then the method loops back to monitor cardiac output (block 602). However, if there is still a high heart rate, then the process progresses from ATP to a shock, at block 624. At this point in the method, the process flow has encountered the presence of cardiac output with a higher than normal heart rate that is not responsive to either atrial ATP or ventricular ATP. The method 600 assumes that the safest therapy for dealing with the conditions detected thus far is to deliver an atrial shock, such as a low pain, high energy atrial shock. To administer the shock an exemplary ICD 200 executing the method 600 may use an RA electrode, such as right atrial ring electrode 321, superior vena cava (SVC) coil electrode 334, etc. The return electrode can be, for example, the RV coil 332, an LV electrode, even the case 400, etc. After the low pain atrial shock, the method 600 returns to monitoring the cardiac output at block 602.

Thus, the exemplary method 600 uses the information that is available to deliver the therapy that provides the best cost/benefit tradeoff, rather than focusing too narrowly on the exact classification of cardiac rhythm.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
    sensing a cardiac output parameter;
    sensing an arterial pressure parameter;
    processing the cardiac output parameter to determine a need for delivering a shock; and
    delivering an initial shock at an energy level to the heart, where the energy level of the initial shock varies as a function of the arterial pressure parameter.

2. The method of claim 1 wherein:
    delivering the initial shock comprises delivering a first shock at a first energy level if the cardiac output parameter indicates insufficient cardiac output and the arterial pressure parameter is below a threshold, and delivering a second shock at a second energy level lower than the first energy level to the heart if the arterial pressure parameter is equal to or above the threshold.

3. The method as recited in claim 2, wherein the threshold comprises a pressure of approximately 60 millimeter of mercury.

4. The method as recited in claim 2, wherein the first energy level possesses an energy in the range of approximately 25 joules to approximately 40 joules and the second energy level possesses an energy in the range of approximately 5 joules to approximately 17 joules.

5. The method as recited in claim 2, wherein delivery of the first shock or the second shock uses a low-pain waveform.

6. The method as recited in claim 1, further comprising repeating the sensing of the cardiac output parameter if the cardiac output parameter indicates that sufficient cardiac output is present.

7. The method as recited in claim 1, wherein the sensing the cardiac output parameter is performed by an implanted device.

8. The method as recited in claim 7, wherein the implanted device comprises a cardiac output sensor that measures an aortic distension.

9. The method as recited in claim 1, wherein the sensing an arterial pressure is performed by an implanted device.

10. The method as recited in claim 9, wherein the implanted device comprises an arterial pressure sensor that combines photoplethysmography with measuring a right ventricular pressure.

11. An implantable system comprising:
    means for sensing cardiac output and arterial pressure parameters of a heart;
    means for deciding to shock the heart based on the cardiac output; and
    means for shocking the heart with an initial shock at an energy level wherein the energy level of the initial shock varies as a function of the arterial pressure.

12. The system as recited in claim 11, further comprising:
    implantable means for sensing a heart rate; and
    implantable means for applying atrial anti-tachycardia pacing to the heart before applying ventricular anti-tachycardia pacing to the heart, if the heart rate is tachycardic.

* * * * *